United States Patent [19]
Roeder

[11] 4,445,900
[45] May 1, 1984

[54] TABLESS SANITARY NAPKIN

[75] Inventor: Robert J. Roeder, Outagamie County, Wis.

[73] Assignee: Kimberly-Clark Corporation, Neenah, Wis.

[21] Appl. No.: 376,484

[22] Filed: May 10, 1982

[51] Int. Cl.³ .............................................. A61F 13/16
[52] U.S. Cl. .................................... 604/389; 604/390
[58] Field of Search ................................. 604/389, 390

[56] References Cited

U.S. PATENT DOCUMENTS 3,672,371  6/1972  Roeder ................................. 604/390

Primary Examiner—C. Fred Rosenbaum
Assistant Examiner—Sherri E. Vinyard
Attorney, Agent, or Firm—Howard Olevsky; R. Jonathan Peters; Gregory E. Croft

[57] ABSTRACT

A sanitary napkin as provided having an adhesive pattern in the form of an X with the crossing portion of the X located at the approximate center of the napkin.

2 Claims, 1 Drawing Figure

TABLESS SANITARY NAPKIN

FIELD OF THE INVENTION

This invention relates to tabless sanitary napkins and particularly to an improved adhesive pattern for these napkins.

BACKGROUND OF THE INVENTION

Since their introduction, sanitary napkins with adhesive attachment means, i.e., the so-called tabless sanitary napkins have proven to be a dominant force in the marketplace. Previous to the introduction of sanitary napkins having adhesive attachment means, napkins were constructed with long extensions at either ends called tabs. These tabs were attached to separate belts. The tabless sanitary napkins due to obvious advantages of convenience and comfort have almost universally supplanted these belted napkins.

While this shift in consumer preference has taken place in little more than a decade, there has been continuing effort directed towards developing a superior adhesive pattern which would provide secure attachment to undergarments and ease of release without either tearing the napkin or leaving substantial adhesive residue in the undergarment itself.

The most widely used and accepted pattern is that described in U.S. Pat. No. 3,672,371 issued to me, which provides for at least two centrally disposed narrow parallelly spaced lines of garment attachment adhesive. This pattern has been substantially, universally accepted and while the art is replete with attempts to design alternative configurations, the majority of the sanitary napkins currently sold in the United States utilize this configuration.

As discussed in my prior patent, a sanitary napkin during use is subjected to shear stress and other forces such as rotational torque applied to the napkin during movement by the wearer. It has been recognized, in fact, that the napkin will, during wear, actually become unattached and then reattach itself.

It has also been recognized that the napkin is subjected to side crushing forces which tend to permanently distort the napkin along each longitudinal edge. This crushing of the napkin can in some cases not only dislodge the napkin from its adhesive mooring, but can also distort the back surface of the napkin in such a manner as to provide for the contact of the centrally disposed adhesive lines with each other and therefor prevent the napkin from reattachment to the undergarment of the wearer.

While there are several different prior art configurations for adhesive pattern positioning, as for example disclosed in U.S. Pat. Nos. 3,575,175; 3,888,255; 3,897,783; and 3,973,567 or as set out in the prior art figures of U.S. Pat. No. 3,672,371 none of the prior art configurations provide the advantages of the pattern disclosed and claimed therein.

SUMMARY OF THE INVENTION

According to this invention a sanitary napkin is provided having thin adhesive lines which converge and intersect at the approximate center of the napkin to form an X pattern. This pattern provides for excellent attachment to the wearer's garment, but eliminates the possibility of the adhesive lines attaching to each other during wear.

DETAILED DESCRIPTION OF THE INVENTION

Figure 1:
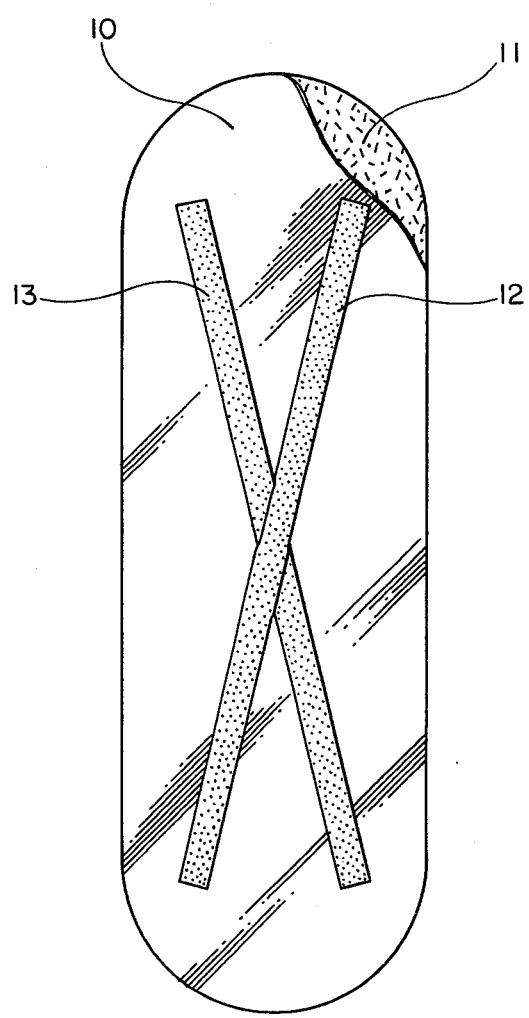

The invention can be more readily understood by reference to the drawings in which FIG. 1 is a bottom plan view partially in cross-section of the invention.

According to FIG. 1, a sanitary napkin having an absorbent 11 and a fluid impervious baffle 10 attached thereto has an adhesive pattern represented by lines 12 and 13 which cross in the approximately center of the napkin to form an X configuration. It is preferred that the edges of the X terminate at least 0.4 inches from the edge of the napkin so that there is a minimum possibility of attachment by the adhesive directly to the napkin wearer. The adhesive pattern of this invention can be designed so that an extremely small amount of adhesive can provide substantial attachment.

The sanitary napkin described previously has only an absorbent batt and a fluid impervious baffle. It is to be understood that the batt can be wrapped with a fluid permeable wrap and that the wrap itself may overlap either around the bottom of the baffle or between the baffle and the absorbent batt. Where the wrap overlaps on the bottom, i.e., garment facing side of the baffle, the adhesive lines will be positioned on the wrap and, as disclosed in U.S. Pat. No. 3,672,371 may actually be used to seal the overlap portion.

What is claimed is:

1. A sanitary napkin having adhesive attachment means comprising fluid absorbent batt adapted to be in absorbent contact with the wearer and a fluid impermeable baffle to position toward the garment facing side said attachment means consisting of an adhesive attachment pattern in the form of an X with the crossing portion of the X located in the approximate center portion of the napkin.

2. A sanitary napkin according to claim 1 where the ends of the adhesive pattern terminate at least 0.4 inches from the edges of the napkin.

* * * * *